United States Patent
Fitzpatrick

(10) Patent No.: US 9,687,347 B2
(45) Date of Patent: Jun. 27, 2017

(54) PERCUTANEOUS IMPLANT

(71) Applicant: FITZBIONICS LIMITED, Eashing (GB)

(72) Inventor: Martin Noel Fitzpatrick, Surrey (GB)

(73) Assignee: FITZBIONICS LIMITED, Surrey (GB)

( * ) Notice: Subject to any disclaimer, the term of this patent is extended or adjusted under 35 U.S.C. 154(b) by 0 days.

(21) Appl. No.: 14/438,456

(22) PCT Filed: Oct. 10, 2013

(86) PCT No.: PCT/GB2013/052639
§ 371 (c)(1),
(2) Date: Apr. 24, 2015

(87) PCT Pub. No.: WO2014/064420
PCT Pub. Date: May 1, 2014

(65) Prior Publication Data
US 2015/0289978 A1 Oct. 15, 2015

(30) Foreign Application Priority Data

Oct. 26, 2012 (GB) .................................. 1219316.5

(51) Int. Cl.
*A61F 2/28* (2006.01)
*A61F 2/78* (2006.01)
(52) U.S. Cl.
CPC .................. *A61F 2/28* (2013.01); *A61F 2/78* (2013.01); *A61F 2002/7887* (2013.01); *A61F 2230/0069* (2013.01)

(58) Field of Classification Search
CPC ...... A61F 2/78; A61F 2/2814; A61F 2/30749; A61F 2002/7887; A61F 2002/464;
(Continued)

(56) References Cited

U.S. PATENT DOCUMENTS 7,014,661 B2 * 3/2006 Blunn .................. A61C 8/0018
623/11.11
2007/0260312 A1 * 11/2007 Grundei ................ A61F 2/2814
623/16.11
(Continued)

FOREIGN PATENT DOCUMENTS

ES 2138133 A1 * 12/2009 .......... A61F 2/2814
WO 0238083 5/2002

OTHER PUBLICATIONS

International Search Report and Written Opinion in copending, related PCT Application No. PCT/GB2013/052639, mailed Feb. 21, 2014.

*Primary Examiner* — Christian Sevilla
*Assistant Examiner* — Megan Wolf
(74) *Attorney, Agent, or Firm* — Thomas | Horstemeyer, LLP

(57) ABSTRACT

A percutaneous implant (10) comprises a bone-fixation portion (20), a spigot portion (50) for the attachment of an external prosthesis, and a pear-shaped portion (40) having a porous outer region (44) comprising a mesh of wire mesh material around a central core. The portion (40) is disposed between the spigot portion (50) and a collar (30) which has a plurality of through holes (34) adjacent to its edge. The bone-fixation portion (20) may have extending parallel thereto a plate (72) for attachment to the side of a bone.

13 Claims, 2 Drawing Sheets

(58) Field of Classification Search
CPC .. A61F 2002/30912; A61F 2002/30622; A61F 2002/4228–2002/4235; A61F 2002/4243–2002/4248
See application file for complete search history.

(56) References Cited

U.S. PATENT DOCUMENTS

| | | | |
|---|---|---|---|
| 2008/0195219 A1* | 8/2008 | Wiley | A61F 2/4241 623/21.11 |
| 2008/0200995 A1 | 8/2008 | Sidebotham | |
| 2011/0029002 A1* | 2/2011 | Mann | A61B 17/60 606/151 |
| 2011/0190907 A1* | 8/2011 | Porter | A61F 2/78 623/32 |

* cited by examiner

PERCUTANEOUS IMPLANT

CROSS-REFERENCE TO RELATED APPLICATION

This application is the 35 U.S.C. 4371 national stage of, and claims priority to and the benefit of, PCT application PCT/GB20131052639, filed Oct. 10, 2013, which claims priority to and the benefit of GB Application No. 1219316.5, filed on Oct. 26, 2012, herein incorporated by reference in their entireties.

The present invention relates to percutaneous implants and in particular to implants to which external prostheses can be attached. Implants according to the present invention are particularly suitable in connection with partially-amputated limbs or digits in humans and animals.

Aspects of the present invention seek to provide an improved implant. Aspects of the present invention seek to provide an implant with a suitable location for muscle or other tissue attachment. Aspects of the present invention seek to provide an implant with suitable support for and interaction with the skin surrounding the implant.

According to a first aspect of the present invention there is provided a percutaneous implant comprising a bone-fixation portion and a spigot portion with an enlarged portion therebetween, said enlarged portion having a porous region at least over part of its surface.

An advantage of the above arrangement is that, after deployment of the implant, the bulbous portion maintains a desired disposition between the bone, the skin and other body tissues. The skin can satisfactorily seal around the junction between the spigot portion and the bulbous portion. Muscles and other tissues can grow around the part of the bulbous portion closer to the bone-fixation portion.

The porous region allows fluid to enter the surface of the bulbous portion to a limited depth.

An advantage of this arrangement is that, on the one hand, tissue regrowth is encouraged while, on the other hand, fluid cannot enter the bulbous portion into regions where it might stagnate and cause infection.

The bulbous portion can be configured to be porous by providing a mass of wire mesh material around a central dome, rod or other core part.

According to a second aspect of the present invention, there is provided a percutaneous implant comprising a bone-fixation portion and a spigot portion with a bulbous portion therebetween.

The bulbous or enlarged portion is preferably pear-shaped, with the broad part of the pear being towards the spigot portion. The bulbous or enlarged portion preferably merges into the spigot portion via a concave surface region.

In preferred arrangements, the bulbous or enlarged portion merges smoothly into a collar portion, preferably via a concave surface region.

The collar is preferably configured to be substantially disc-shaped, with inclined edge regions and a plurality of through holes or perforations adjacent to the edge regions. An advantage of the disc shape is that, upon deployment of the implant, it abuts against a patient's bone to provide stability and to reduce damage to the bone. An advantage of the configuration of the edge regions of the collar is that they encourage tissue regrowth.

The collar may have a through hole substantially larger than the other holes for the passage of a screw for attachment to a bone.

A plate member may be attached to the implant in the region of the collar. The plate member may extend generally parallel to the stem portion and have a plurality of through holes for attachment to the bone after deployment.

The stem portion may have a plurality of fin elements projecting from at least part of its length. The fin elements serve to prevent rotation relative to the bone after deployment.

Preferred embodiments of the present invention will now be described, by way of example only, with reference to the accompanying drawings, of which:

Figure 1:
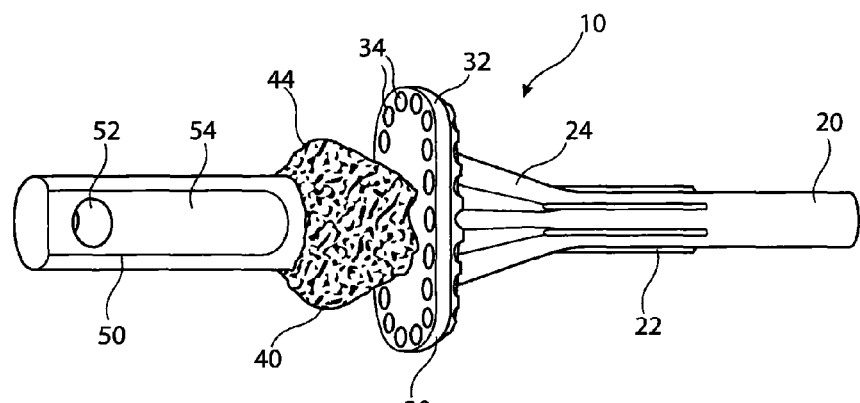
FIG. 1 is a side view of a percutaneous implant in accordance with a first embodiment of the present invention.

Referring to the drawings, FIG. 1 shows a side view of an implant 10 comprising a bone-fixation portion in the form of an intramedullary stem 20, a collar 30, a bulbous portion 40 which is substantially pear-shaped, and a spigot portion 50.

Stem portion 20 is configured to fill the medullary cavity of a bone and to provide close cortical contact. The stem is provided with projecting fins 22 to prevent rotation relative to the bone. The proximal end 24 of the stem tapers outwardly to collar 30 which forms an enlarged plateau.

Collar 30 is configured to provide an abutment for the resected bone providing axial load transfer onto the cortical bone thus reducing shear stress in the bone surrounding the stem. The outer diameter of the plateau is generally maintained in line with the cortical girth with an angled edge 32 with through holes or perforations 34 to allow attachment of muscles. This is intended to enhance implant loading whilst providing muscle attachment for a near normal function. It will be noted that collar 30 is substantially in the form of a disc.

Figure 2:
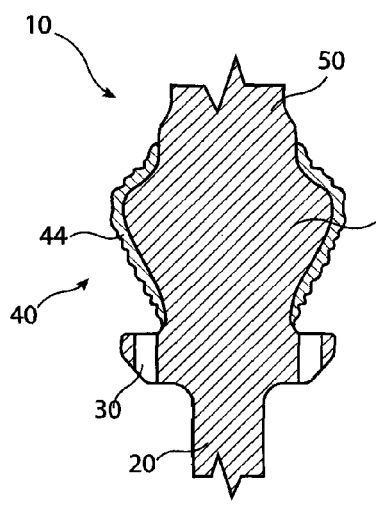
FIG. 2 is an enlarged cross-sectional view of part of the central region of the implant.

Collar 30 is followed by pear-shaped portion 40 which has a solid core or dome 42, FIG. 2, the surface of which has a porous outer region 44. The porous structure is provided by applying wire mesh material e.g. 1-2 mm mesh, around a central dome. The pore structure and size of region 44 encourage dermal tissue ingrowth. As shown in FIG. 2, region 44 does not extend deeply into core 42 which is shaped to conform to the region 44.

To the end of the portion 40 remote from collar 30 there is connected a spigot portion 50 which is aligned with stem portion 20. The spigot has a through hole 52 and one or more flat surfaces 54 to permit the attachment of an exo-prosthesis, such as a prosthetic limb of plastic or carbon fibre material.

The cross-sectional area of the bulbous portion 40 is enlarged compared to the cross-sectional areas of stem 20 and spigot 50.

The whole implant 10 is integrally constructed of titanium alloy material using a direct metal laser sintering (DMLS) production process and is heat treated to give optimal strength. The spigot portion 50 is subsequently precisely machined to fit an exo-prosthesis.

Selected regions of the implant 10 are then provided with a hydroxyapatite (HA) coating to promote bone enticement and dermal tissue ingrowth. In a preferred arrangement, the stem portion 20 and collar 30 are coated in this way. The implant 10 is first shot-blasted for rough texture in the regions where the HA coating is to be applied followed by the application of a 50-100 micrometer thick HA coating using plasma deposition process. Prior to the application of HA coating but after shot-blasting the implant may be treated for silver impregnation onto the entire surface, the silver having an antibacterial property suitable for this skin portal device. Fibronectin may also be applied to the HA as a secondary coating to promote osteoblast and fibroblast adhesion to promote rapid implant integration and recovery.

Figure 3:
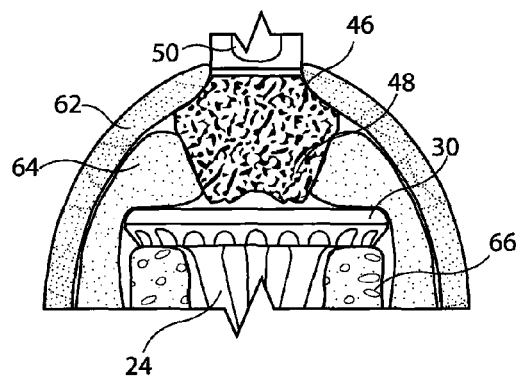
FIG. 3 is a view of the central region of the implant after deployment.

FIG. 3 shows the implant 10 after percutaneous deployment into a bone 66 of a human or animal, and in particular the disposition of the various parts of bulbous portion 40 relative to the deployment site. It will be noted that the top 46 of portion 40 has a shape similar to that of an umbrella which allows the skin 62 to sit over the top whilst the rough and porous region 44 allows tissues to grow into the pores firmly fixing and sealing the implant interface. The contoured profile allows the skin to be placed tightly against the implant without creating voids underneath, whilst providing a porous membrane around the spigot 50 for it to grip on. This anchoring around the spigot prevents skin pulling away from the spigot potentially opening the interface leading to failure and/or infection. The angular slope is configured to provide graduated support by facilitating the correct orientation for optimal attachment. The solid core 42 extends beyond the outer layer of skin 62 where it merges with spigot 50.

The curving of the junction between the portions 40 and 50 serves to prevent cavitation under the skin.

The lower part 48 of portion 40 is configured to allow positioning and attachment of muscle tissues and ligaments 64 thereto. The porous region 44 around portion 40 is limited in depth for the tissues to grow into without leaving cavitation which if present might create stagnant conditions possibly encouraging infection. Attachment of the muscle tissues around the portion 40 also produces a soft fill under the skin supporting it and preventing the skin from looseness, sharp bends and abnormal loading.

After deployment of the implant, and possibly after a period of time for ingrowth of the bone and soft tissue, a suitable exo-prosthesis is attached to spigot 50. The exo-prosthesis can be fitted with a quick release mechanism for ease of prosthesis removal when not required.

Preferred dimensions of the implant for small animals are: diameter of stem between 4 and 10 mm, most preferably 5 to 9 mm; length of stem 40 mm to 70 mm, most preferably 45 to 60 mm; thickness of collar 4 mm; height of bulbous portion between 10 and 20 mm, most preferably 15 mm; length of spigot 30 mm. In one preferred embodiment, the stem 20 has a diameter of 6 mm and a length of 49 mm. In another preferred embodiment, the stem has a diameter of 8 mm and a length of 57 mm.

Increased dimensions are used in implants for larger animals and humans so as to be appropriate for larger loads.

The above-described arrangement has numerous advantages. The bulbous portion 40 serves to strongly support the load generated by an exo-prosthesis when attached to spigot 50. The integral nature of the implant 10 provides a robust fixation for the exo-prosthesis to the bone 66. With this device, the exo-prosthesis has no direct contact with the skin 62 thus eliminating pressure related sores, skin tears and obstruction to sweat glands normally associated with the other methods of attachment for an exo-prosthesis.

The attachment of muscles adjacent to the portion 40 provides a soft support for the dermal layer whilst the honeycomb layer provides a rigid structure for mechanical ingrowth for the dermis stabilising it to form a sustainable skin/implant seal against infection and ingress.

The abutment collar 30 acts as a platform against which abuts the cylinder of the bone cortex; this reduces any tendency of the stem 20 to split the bone 66. The perforation of the edges 32 of the collar allows tendon and soft tissue attachment and also promotes bone ingrowth. The holes or perforations 34 can also be used for the attachment of sutures during the deployment procedure.

The coating of parts of the implant 10 with hydroxyapatite encourages soft tissue ingrowth leading to structural integration and a physical seal against the implant surface.

The provision of fins 22 prevents rotation of the inserted implant relative to bone 66 and enables optimal bending and torsional stability.

The use of titanium alloy produces an implant with high fatigue strength and durability.

Various modifications can be made to the above-described arrangement. In particular, portion 40 may have any suitable solid shape; for example it may be shaped like a bulb or like a strawberry. Alternatively it may be generally spherical, part-spherical, cylindrical, ellipsoidal, part-ellipsoidal, pyrimidical etc. The top 46 of portion 40 may be generally frusto-conical or flat, but such arrangements are less efficient in interacting with and providing a good seal with the skin. The bottom 48 of portion 40 may be generally cylindrical or frusto-conical, but such arrangements are less efficient in interacting with and attachment to body tissues.

The portion 40 may be provided with a porous region 44 over only a part of its surface, for example only over its top part 46 or only over its bottom part 48. The porous structure may be provided in different ways from a wire mesh. For example, it may comprise a honeycomb arrangement or a hexagonal, three-dimensional matrix. To facilitate bone entry, the pore size is preferably in the range 0.5 mm to 2 mm and most preferably 0.7 mm to 1 mm. An array of dimples can be provided. Alternatively, a region with small interconnecting passageways, circular interlocking pores, and/or a plurality of cavities can be provided.

Figure 4:
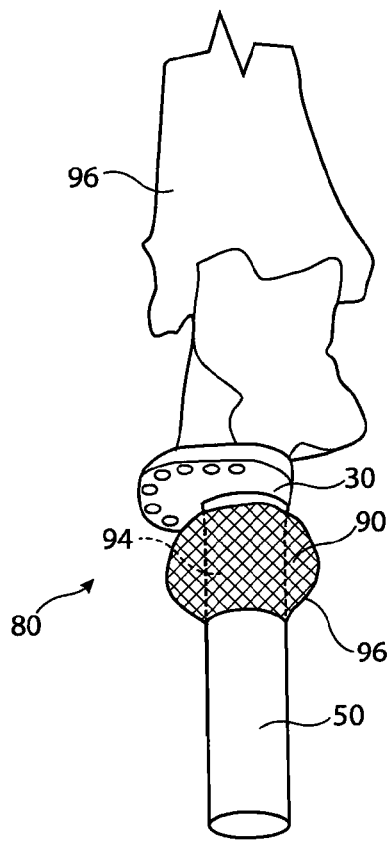
FIG. 4 is a perspective view of an implant in accordance with a second embodiment of the present invention deployed in a bone.

FIG. 4 shows an implant 80 in which the bulbous portion 90 comprises as the porous region a mass of wire mesh material 96 applied around a central rod 94 which is aligned with spigot 50. In this embodiment, the collar 30 has an irregular outline and is located excentrically of the spigot 50 and the stem (not shown).

The spigot 50 of this embodiment does not have a through hole.

As shown in FIG. 4, the bone is the ankle bone (calcaneus) of a dog. An advantage of the present implant is being able to locate the implant below a joint rather than above it, thus allowing the patient greater freedom of movement.

Whatever the nature of the porous region 44, 96, the HA coating is applied as an additional step.

As shown, collar 30 is of generally oval shape. However, it may have any desired shape including circular, rectangular, polygonal or irregular. It may be symmetrical or asymmetrical. As shown, it is located generally centrally relative to stem 20, but in modifications it can be located off-centre. The holes 34 in the collar may be of any desired size and pattern. If desired, collar 30 can be omitted.

In certain modifications, the functions of the collar 30 and bulbous portion 40 can be combined into a generally disc-shaped, e.g. discus-shaped, portion; this disc-shaped portion is then provided with the porous surface structure.

For certain applications, stem 20 and spigot 50 are not aligned but are offset and/or oriented at an angle relative to each other.

Instead of, or in addition to, fins 22 the stem 20 may be provided with one or more grooves to grip the bone. Instead, or in addition, the stem 20 may be provided with one or more roughened areas to produce irregularities to interlock with the bone 66.

The HA coating may extend only part of the way along stem 20 from its free end. The coated portion entices bone contact, whereas the uncoated portion provides toggling support and reduces the possibility of necking through stress shielding, thus prolonging the working life of the implant 10.

In another modification the HA coating covers the entire stem 20, collar 30 and bulbous portion 40; the combination of the HA coating and the porous layer 44, 96 promotes tissue ingrowth and a physical seal in this region. Each of the patterns of coating the implant with HA material has its own advantages for controlling the stresses transferred between the implant and the bone in use.

Any suitable mineral or biological augmenting material may be used instead of, or in addition to, HA as a coating material. In other modifications, the coating can be completely omitted.

Any suitable metallic or synthetic material can be used instead of titanium alloy to manufacture the implant 10. A memory alloy such as nickel titanium alloy can be used. Although described as an integral member, it can comprise suitable components attached to each other.

Figure 5:
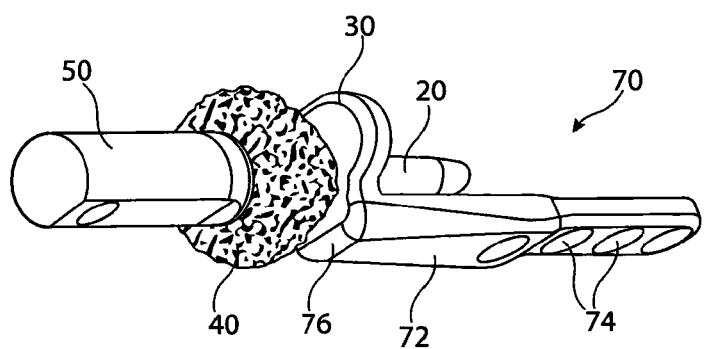
FIG. 5 is a side view of a percutaneous implant in accordance with a third embodiment of the present invention.

FIG. 5 shows an implant 70 which in addition to stem 20 has a cortical plate 72 extending generally parallel to the stem. The plate 72 is integrally attached to the implant in the region of collar 30. The plate 72 has a plurality of through holes 74 for attachment to the side of bone 66.

Plate 72 provides additional security against the effects of torsion and also for immediate stability at implantation. This has the advantage of allowing the attachment of an exo-prosthesis to be fitted immediately after deployment without needing to wait for bone and soft tissue ingrowth. This advantage applies even to weight-bearing limbs.

Figure 6:
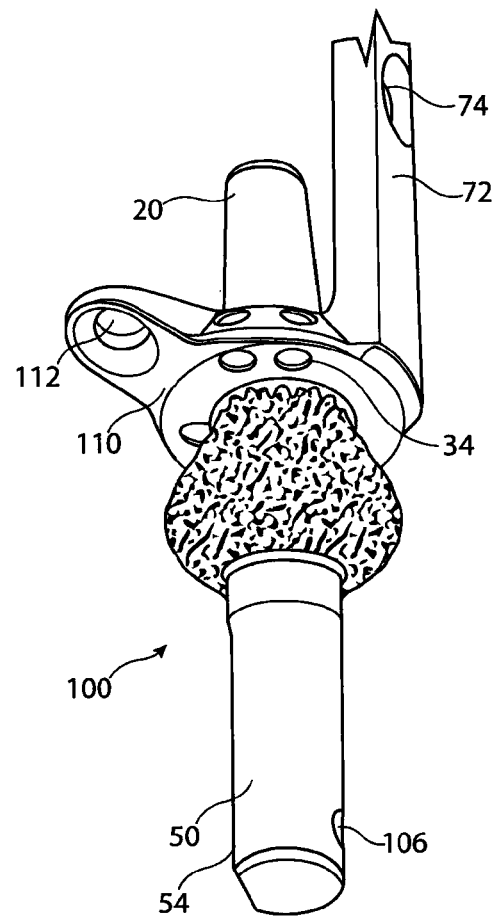
FIG. 6 is a view similar to FIG. 5 of a fourth embodiment of the present invention.

FIG. 6 shows an implant 100 in which the parts of the implant 70 are supplemented by a flange 110 having a hole 112 for a screw (not shown) for attachment to a bone. The particular implant shown is for deployment below an ankle joint, with stem 20 entering the calcaneus and with the screw through hole 112 being attached to the talus. In this embodiment there is a reduced number of holes 34 through the flange for the attachment of muscles. In addition spigot 50 has no through hole 52, but instead a circular recess or notch 106 for clamping on a suitable exo-prosthesis. The recess 106 is on the side of spigot 50 opposite to flat surface 54.

Implants similar to implant 100 can be used in any similar application to a two bone construct, for example the radius and the ulna.

Implants in accordance with the above-described embodiments can be used in connection with the femur, tibia, radius, humerus, phalynx or other suitable bone. They can be applied in all situations in which there is functional or aesthetic deficiency which can be compensated for by an application of an exo-prosthesis.

The features and modifications of the described arrangements may be combined or interchanged as desired.

The invention claimed is:

1. A percutaneous implant comprising a bone-fixation portion and a spigot portion with an enlarged portion therebetween, and a collar portion between the enlarged portion and the bone-fixation portion and adjoining both the enlarged portion and the bone-fixation portion, wherein the collar portion is radially projecting beyond adjoining parts of both the enlarged portion and the bone fixation portion, wherein the enlarged portion merges smoothly into said collar portion via a concave curved surface and wherein the enlarged portion merges into the spigot portion via a concave surface region with a curved junction between the enlarged portion and the spigot portion, said enlarged portion having a porous region or layer over at least part of its surface, which allows fluid to enter the surface of the enlarged portion to a limited depth and wherein the enlarged portion comprises a mass of wire mesh material around a central core.

2. An implant according to claim 1, wherein the collar portion is configured to be substantially disc-shaped.

3. An implant according to claim 1, wherein the collar portion has edge portions which are inclined.

4. An implant according to claim 1, wherein the collar portion has a plurality of holes adjacent to its edge regions.

5. A percutaneous implant comprising a bone-fixation portion and a spigot portion with an enlarged portion therebetween, the enlarged portion being pear-shaped, with a broad part of the pear being towards the spigot portion and a collar portion between the enlarged portion and the bone-fixation portion, wherein said collar portion is radially projecting, and wherein the enlarged portion merges smoothly into said collar portion via a concave curved surface, and merges into the spigot portion via a concave curved surface, said enlarged portion having a porous region at least wherein the over part of its surface wherein the bone-fixation portion, the spigot portion and the enlarged portion are integrally formed with each other.

6. An implant according to claim 5, wherein the collar portion is configured to be substantially disc-shaped.

7. An implant according to claim 5, wherein the collar portion has edge portions which are inclined.

8. An implant according to claim 5, wherein the collar portion has a plurality of holes adjacent to its edge regions.

9. An implant according to claim 5, having a plate member attached thereto which extends generally parallel to the bone-fixation portion, the plate member being spaced apart from the bone-fixation portion for attachment to the side of a bone.

10. An implant according to claim 5, wherein the bone-fixation portion has a plurality of fin elements projecting from at least part of its length.

11. An implant according to claim 5, wherein the enlarged portion comprises a mass of wire mesh material.

12. An implant according to claim 5, wherein the enlarged portion comprises a mass of wire mesh material around a central core.

13. An implant according to claim 5, wherein the porous region allows fluid to enter the surface of the enlarged portion to a limited depth.

* * * * *